| (12) | United States Patent | (10) Patent No.: | US 9,128,049 B2 |
|---|---|---|---|
| | Groz et al. | (45) Date of Patent: | Sep. 8, 2015 |

(54) SENSOR SYSTEM AND METHOD FOR DETERMINING AN OPTICAL PROPERTY OF A PLANT

(71) Applicant: Franke GmbH, Aalen (DE)

(72) Inventors: Daniel Groz, Aalen (DE); Guenter Dittmar, Aalen (DE)

(73) Assignee: FRANKE GMBH, Aalen (DE)

( * ) Notice: Subject to any disclaimer, the term of this patent is extended or adjusted under 35 U.S.C. 154(b) by 126 days.

(21) Appl. No.: 13/764,869

(22) Filed: Feb. 12, 2013

(65) Prior Publication Data

US 2013/0152464 A1 Jun. 20, 2013

Related U.S. Application Data

(63) Continuation of application No. PCT/EP2011/062102, filed on Jul. 14, 2011.

(30) Foreign Application Priority Data

Aug. 13, 2010 (DE) .......................... 10 2010 034 603

(51) Int. Cl.
*G01N 21/00* (2006.01)
*G02B 26/00* (2006.01)
*G01N 21/55* (2014.01)
(Continued)

(52) U.S. Cl.
CPC ...... *G01N 21/55* (2013.01); *A01G 7/00* (2013.01); *G01N 21/3151* (2013.01); *G01N 21/474* (2013.01); *G01N 2021/8466* (2013.01)

(58) Field of Classification Search
USPC ........................................................ 356/445
See application file for complete search history.

(56) References Cited

U.S. PATENT DOCUMENTS 4,804,850 A 2/1989 Norrish et al.
5,296,702 A * 3/1994 Beck et al. .................... 250/226

(Continued)

FOREIGN PATENT DOCUMENTS

DE 10 2008 005 191 A1 7/2008
EP 1 125 111 B1 8/2001

(Continued)

OTHER PUBLICATIONS

Fei Li et al.; Estimating N status of winter wheat using a handheld spectrometer in the North China Plain; Nov. 2007; 9 pp.

(Continued)

*Primary Examiner* — Michael A Lyons
*Assistant Examiner* — Jarreas C Underwood
(74) *Attorney, Agent, or Firm* — Harness, Dickey & Pierce, P.L.C.

(57) ABSTRACT

A sensor system for determining an optical property of a plant by means of a reflection measurement, having a first light source, which emits light along a first beam axis, and a second light source, which emits light along a second beam axis, and at least one receiver, which is aligned along a third beam axis, to detect light reflected from the plant. The first light source, the second light source, and the receiver are arranged relative to one another so that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle ($\alpha$, $\delta$) with the third beam axis. Related methods are also disclosed.

18 Claims, 6 Drawing Sheets

(51) Int. Cl.
*G01N 21/31* (2006.01)
*G01N 21/47* (2006.01)
*A01G 7/00* (2006.01)
*G01N 21/84* (2006.01)

(56) References Cited

U.S. PATENT DOCUMENTS

| | | | | |
|---|---|---|---|---|
| 5,389,781 A | * | 2/1995 | Beck et al. | 250/226 |
| 5,754,296 A | * | 5/1998 | Law | 356/369 |
| 5,789,741 A | * | 8/1998 | Kinter et al. | 250/226 |
| 5,837,997 A | * | 11/1998 | Beck et al. | 250/227.11 |
| 5,959,451 A | * | 9/1999 | De Torfino | 324/236 |
| 6,020,587 A | * | 2/2000 | Spiering et al. | 250/339.11 |
| 6,443,365 B1 | * | 9/2002 | Tucker et al. | 239/69 |
| 7,408,145 B2 | * | 8/2008 | Holland | 250/221 |
| 8,179,533 B2 | * | 5/2012 | Alameh | 356/445 |
| 8,228,504 B2 | * | 7/2012 | Galtie et al. | 356/432 |
| 8,537,337 B2 | * | 9/2013 | Welty | 356/4.01 |
| 8,654,319 B2 | * | 2/2014 | Rao et al. | 356/73 |
| 2005/0098713 A1 | | 5/2005 | Holland | |
| 2006/0102851 A1 | | 5/2006 | Jalink et al. | |
| 2008/0239293 A1 | | 10/2008 | Fuchigami et al. | |

FOREIGN PATENT DOCUMENTS

| | | |
|---|---|---|
| JP | 2004-294075 | 10/2004 |
| WO | WO 94/02812 | 2/1994 |
| WO | WO 02/088679 A1 | 11/2002 |
| WO | WO 2006/007883 A1 | 1/2006 |
| WO | WO 2007/062196 A2 | 5/2007 |

OTHER PUBLICATIONS

Anatoly A. Gitelson et al.; Nondestructive Estimation of Anthocyanins and Chlorophylls in Anthocyanic Leaves; Oct. 2009; 8 pp.
International Search Report for PCT/EP2011/062102; mailed Oct. 20, 2011; 5 pp.
English language translation of International Preliminary Report on Patentability (Chapter 1); issued by WIPO Feb. 28, 2013; 7 pp.
English translation of European Examination Report for Appl'n. No. 11 743 471.2 dated Jul. 10, 2015; 9 pp.

* cited by examiner

SENSOR SYSTEM AND METHOD FOR DETERMINING AN OPTICAL PROPERTY OF A PLANT

CROSS-REFERENCE TO RELATED APPLICATIONS

This is a continuation application of International patent application PCT/EP2011/062102, filed Jul. 14, 2011, which was published in German and claims the priority of German patent application DE 10 2010 034 603.9, filed Aug. 13, 2010. The entire contents of these priority applications are incorporated herein by reference.

BACKGROUND OF THE INVENTION

The present invention relates to a sensor system for determining an optical property, in particular the chlorophyl content or an illness or pest infestation, of a plant or a leaf by means of a reflection measurement, having a first light source, which emits light along a first beam axis, and a second light source, which emits light along a second beam axis, and at least one first receiver, which is aligned along a third beam axis, to detect light reflected from the plant.

Furthermore, the present invention relates to a corresponding method for determining an optical property of a plant, in particular the chlorophyl content or an illness or pest infestation.

Finally, the present invention relates to a method for analyzing a measurement to determine an optical property of a plant, in particular the chlorophyl content or an illness or pest infestation.

The fertilization of green plants using nitrogen is widespread in agriculture. During photosynthesis, nitrogen is used, inter alia, for the purpose of producing proteins. In this manner, the nitrogen promotes the growth of the plants. To allow the plants to absorb the nitrogen, fertilization is performed using an ammonium or nitrate salt. The farmer has to ensure an optimum nitrogen content of the plants, since both a lack of nitrogen and also an excess of nitrogen can impair the development of the plants. A lack of nitrogen is typically expressed in a lack of growth, a pale green color of the leaves, excessively early blooming, and yellowing of the plant. A nitrogen excess can result in lush growth, dark green leaves, delayed blooming, and spongy and soft leaf tissue. In addition, plants having nitrogen excess are frequently susceptible to frost and illness. For farmers, it is therefore desirable to be able to measure the nitrogen content of the plants in a field, in order to make a decision about the fertilization to be performed. In addition, the soil and the groundwater can thus also be prevented from being stressed with excessive fertilizer.

In particular, it is desirable in this case to be able to determine the nitrogen content in a contactless manner. Methods in which plant parts are clamped in measuring apparatuses or plants are pulverized and analyzed by means of chemical methods are excessively cumbersome and time-consuming for daily use and usage in the field. An example of this is found in the document US 2008 0239293 A1. Therefore, a demand exists in the market merely for contactless, in particular optical, measuring methods.

Nitrogen atoms do not display any absorption bands for optical radiation. The nitrogen content in the plant can therefore only be determined via an indirect route. Because of the close relationship between the nitrogen content of a plant and the chlorophyl content of a plant, the nitrogen content is determined indirectly via the chlorophyl content of the plant. The chlorophyl content of plants is strongly correlated with proteins of the photosystem, which contain the majority of the plant nitrogen, so that the nitrogen content of a plant can be inferred after a determination of the chlorophyl content.

Various optical methods are in turn known for determining the chlorophyl content.

A fluorescence measurement to determine the chlorophyl content is widespread. A sensor measures a short-term spontaneous emission of fluorescence radiation as a response to a flashing irradiation of the leaves. In this case, an irradiation device excites the molecules in the leaves in the photosynthetically active range using repeated laser flashes. This type of measurement is also called laser-induced fluorescence (LIF). The irradiation is performed using shortwave high-energy radiation, for example light in an orange wavelength range. The response of the chlorophyl-containing leaves is lower-energy radiation having somewhat greater wavelength than the excitation light, for example radiation in the near infrared range. Conclusions about the chlorophyl content of the plant can be drawn from the spectral composition of the fluorescent light. However, the fluorescence measurement has the disadvantage that the measurement can only be carried out on living plants. This is not critical in practice in the field; however, it has the result that, for example, a calibration of the sensors to detect the chlorophyl content must be carried out on living plants. Alternatively, for example, plates which are painted with a specific color cannot be used, wherein the color is to correspond to a specific chlorophyl content of a specific plant, in order to perform the calibration.

Furthermore, the fluorescence properties of plants change over the course of the day. Fluorescence measurements must therefore always be carried out in a predefined time window (for example, between 11 am and noon), so that the calibration and corresponding calculation algorithms apply. Examples of the determination of the chlorophyl content of a plant by means of fluorescence measurement are found, for example, in the documents EP 1 125 111 B1 and DE 60 306 675 T2.

Furthermore, reflection measurement to determine the chlorophyl content is known. A light beam having defined power is emitted onto the plant. The power of the fraction of the light beam reflected from the plant is measured and put in a ratio to the emitted power.

So-called passive optical reflection methods exist, in which daylight is used as the radiation source. However, the sun is a continuous light radiator, whose luminosity changes in a ratio of more than 100,000:1 during the course of the day. Therefore, sensors which use passive optical reflection methods in turn deliver measured values which are dependent on the position of the sun or the time of day, respectively.

Therefore, so-called active optical reflection methods have been developed, which use artificial optical sources, such as lamps, LEDs, or lasers, to irradiate plant parts. The radiation fraction reflected from the plants is analyzed in one or more wavelength ranges and compared to reference values. If green leaves are irradiated with light, they absorb to a large degree the blue light in a wavelength range of less than 480 nm and the red light in a wavelength range of 650 to 680 nm. As a result, the reflection of blue light and red light already saturates at low chlorophyl content. Light around 550 nm and radiation in a red to infrared range from approximately 700 to 730 nm, in contrast, are reflected more strongly, which has the result that they only saturate at a very high chlorophyl content. The higher the chlorophyl content, the lower the reflection at wavelengths around 550 nm and in the wavelength range from 700 to 730 nm.

The reflection values are strongly dependent on the angle between the normal of the leaf and the incidence direction. To determine the absolute chlorophyl content, a comparative value is therefore required, which is obtained from the reflection of red light. The optical power in the spectral range of the red light, i.e., in a wavelength range from 650 nm to 680 nm, is only reflected to a small degree from the plant, and the reflection of this reflected red light is only slightly dependent on the chlorophyl content of the leaf.

Therefore, at least two degrees of reflection are determined at different wavelengths to determine the chlorophyl content. Firstly, the degree of reflection is determined at a wavelength at which the reflection is strongly dependent on the chlorophyl content, for example in the case of green light. This chlorophyl-dependent degree of reflection is compared to a degree of reflection which was measured in a wavelength range which is substantially independent of the chlorophyl content of the plant. Both degrees of reflection are set in a ratio and form a so-called vegetation index, which can be calculated according to a plurality of previously proposed formulas. One example is the formula for the NDVI, in which $$NDVI = \frac{\rho_{grün} - \rho_{rot}}{\rho_{grün} + \rho_{rot}}.$$

A rising chlorophyl content in the leaves results in a reduction of the NDVI value and therefore in a decreasing scale value. In sensor systems which display this NDVI value to an operator, the operator must therefore continuously rethink, since not a higher, but rather a lower NDVI value means a better result. The NDVI values for strongly chlorophyl-containing leaves are at very small numeric values of approximately +0.2 and increase with decreasing chlorophyl fraction to +0.6.

The present invention is concerned exclusively with sensors which operate using an active optical reflection method.

A plurality of sensors for measuring the chlorophyl content are known on the market, which are either implemented as sufficiently small that they can be held in the hand by a person, or have larger dimensions, to be able to be used installed on a tractor, for example.

The measuring fields of the sensors are of different sizes and are established by the optical conditions. Sensors having smaller measuring fields have the disadvantage that they cannot be used alone for the rapid measurement of a larger area. A plurality of individual sensors is then to be used for larger areas, to be able to monitor a strip of a field which is multiple meters wide or the interior of a greenhouse, for example. Such assemblies rapidly become very costly due to the plurality of required sensors, however.

In the tractor-supported systems, for example, the YARA N sensor of Agri Con GmbH is known, which uses an actively measuring fluorescence method. A xenon flash lamp is located on each side of the sensor, which illuminates a strip of approximately 4 m width on each side of the tractor. A sensor sold under the name "MiniVeg N" is also known from Georg Fritzmeier GmbH & Co., which uses an active fluorescence method. A larger strip of field is also actively illuminated here, using a plurality of sensors in the case of the MiniVeg N.

In addition to the applied fluorescence method, these systems have the disadvantage that they must use very high-power light sources to illuminate the large measuring fields simultaneously and uniformly. These light sources not only represent a hazard for the eye safety of the user, i.e., the tractor operator, but rather require complex filter technologies to the emit light only in a non-visible range which still excites the plants, however, for example in the range of 700 nm. These sensors are therefore very costly.

The analysis of the measurement results is always performed via averaging. Since a relatively large area region is irradiated simultaneously, measured values of the radiation reflected from the plants and the radiation reflected from the ground are obtained inseparably and simultaneously during the analysis of the methods. In particular in early growth phases, in which the optimum fertilization state is very important, but the surface vegetation is only 10 to 20%, a relatively large area is therefore to be irradiated as diagonally as possible in the known systems, to be able to measure the most possible green leaf mass and least ground area for reliable averaging. However, young plants only cover the ground to a very small extent. They partially lie flat on the ground or only stand a few centimeters above the ground. Therefore, measuring devices which detect a large area perpendicularly or diagonally often only deliver poor results before the first and therefore most important administration of fertilizer.

Previous systems thus have disadvantages with respect to their dependence on daylight, the measurability of small plants, and the required high light powers. A demand therefore exists for an improved sensor assembly for determining the chlorophyl content of a plant, which remedies the above-described disadvantages.

BRIEF SUMMARY OF THE INVENTION

According to a first aspect of the invention, there is provided a sensor system for determining an optical property of a plant by means of a reflection measurement, having a first light source, which emits light along a first beam axis, and a second light source, which emits light along a second beam axis, and at least one first receiver, which is aligned along a third beam axis, to detect light reflected from the plant, wherein the first light source, the second light source, and the at least one first receiver are arranged relative to one another in such a manner that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle with the third beam axis, wherein the first light source emits light in a first wavelength range and the second light source emits light in a second wavelength range, wherein the first wavelength range is a wavelength range of green light, wherein the second wavelength range is a wavelength range of red light, wherein the first light source and the second light source are arranged in a first housing, and the at least one first receiver is arranged in a second housing, and wherein a fastening of the first light source and of the second light source and of the at least one first receiver is provided such that the angles between the beam axes of the light sources and the beam axis of the at least one receiver and a distance between the light sources and the at least one receiver can be adjusted.

According to a second aspect of the invention, there is provided a sensor system for determining an optical property of a plant by means of a reflection measurement, having a first light source, which emits light along a first beam axis, and a second light source, which emits light along a second beam axis, and at least one first receiver, which is aligned along a third beam axis, to detect light reflected from the plant, wherein the first light source, the second light source, and the at least one first receiver are arranged relative to one another in such a manner that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle with the third beam axis.

An "optical property" is to be understood to include all direct optical properties, but also all indirect optical properties, i.e., properties which can be derived from the direct optical properties. These indirect optical properties include in particular the chlorophyl content and the nitrogen content of the plant. Furthermore, the indirect optical properties also include, however, statements about the infestation of illnesses, fungi, caterpillars, or other pests, since these may be derived in particular from changes of the direct optical properties.

The terms "target cylinder" and "measuring cylinder" refer to the approximate propagation shape of the light beams emitted from the first light source and the second light source. The beam bundles are to have substantially no widening or only very slight widening, for example in a range of 2 mrad. In the case of slight widening, a cone shape of the beam bundles does result, strictly speaking, but the widening is so slight that the beam bundles extend substantially with unchanged cross section along the beam axes and therefore a cylindrical shape of an irradiated spatial region, the target cylinder, substantially results.

It is obvious that the angle between first and third and between second and third beam axes is not zero. The third beam axis is therefore not congruent with the first and the second beam axis. The first beam axis and the second beam axis can be congruent, i.e., can enclose the same angle with the third beam axis; however, they can also enclose different angles with the third beam axis.

The described sensor system offers the advantage that through the precise alignment of the measuring cylinder and the target cylinders, a small region, for example only a section of a leaf of a plant, is irradiated using the first and the second light sources and the reflected radiation of only this section can be received by the at least one receiver. In this manner, it is possible to deviate from the planar irradiation of multiple square meters of a field, in order to perform substantially punctual measurements. Through the arrangement of the beam axes respectively at an angle to one another, it is additionally possible to precisely adjust the sectional plane of the target cylinders and of the measuring cylinder. For example, it is thus possible to adjust them to the average height of the leaves of the plant to be measured. Objects located higher or lower are then not detected during the measurement. In this manner, reflections of other objects, for example the ground, weeds, or other ground coverings, which are located at different height locations, can be excluded from the measurement in a particularly simple manner. Radiation reflected from the ground is no longer incorporated in the measurement result, as is the case, for example, in the case of planar irradiation by lasers having high power.

Finally, the sensor system according to the invention allows the target cylinders and the measuring cylinder to be selected as correspondingly small, so that light sources of lower power can be used. In particular, it is possible to decrease the power of the light sources used sufficiently that corresponding threshold values are not exceeded and the eye safety of the operator is ensured.

According to a third aspect of the invention, there is provided a method for determining an optical property of a plant by means of a reflection measurement, wherein light in a first wavelength range is emitted along a first beam axis by means of a first light source, and light in a second wavelength range is emitted along a second beam axis by means of a second light source, wherein light reflected from the plant is detected by at least one first receiver, which is aligned along a third beam axis, wherein the first light source, the second light source, and the at least one first receiver are arranged relative to one another in such a manner that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle with the third beam axis.

The method according to the third aspect of the invention for determining an optical property of a plant by means of reflection measurement has the same advantages as the sensor system.

In addition to the determination of a chlorophyl content or nitrogen content, respectively, the determination of an optical property can also be used for the purpose of recognizing illnesses of a plant state, for example *Helminthosporium* leaf spot illness on young corn leaves, which can be recognized from light, spindle-shaped spots on the corn leaves. This is necrotic leaf tissue which is no longer available for obtaining nutrients for the plant. However, for example, the aggressive black stem rust fungus (*Puccinia graminis*), which threatens the worldwide wheat stocks, can also be recognized. Because of the relatively high resolution of the proposed sensor system, it is additionally also possible to recognize a pest infestation on leaves, for example caterpillars, maggots, and lice.

According to a fourth aspect of the invention, a method for analyzing a measurement to determine an optical property, in particular the chlorophyl content, of a plant is provided, which has the step of detecting a value pair, which has a spectral reflection coefficient of the plant in a green wavelength range $\rho_{grün}$ and a spectral reflection coefficient of the plant in a red wavelength range $\rho_{rot}$, and the step of determining a normalized logarithmic vegetation index ln $NDVI_{Blatt}$ by means of the equation $$\ln NDVI_{Blatt} = \ln(\rho_{grün} - \rho_{rot}) - \ln(\rho_{rot}),$$

wherein the value pair is discarded at least if the term $\ln(\rho_{grün} - \rho_{rot})$ cannot be determined, and ln $NDVI_{Blatt}$ is calculated if the term $\ln(\rho_{grün} - \rho_{rot})$ can be determined.

Many calculation methods for a vegetation index are found in the literature. Typically, a difference of the reflection coefficients in a first and in a second wavelength range is divided by the sum of the reflection coefficients. The reflection coefficients are to be understood according to the typical definition in optics. They represent the quotient of reflected and incident power.

Only very small measured areas per measurement are detected using the proposed sensor system. Accordingly, many measuring procedures are to be performed, in order to scan an area of a specific order of magnitude.

It is presumed that five valid measured values per square meter must be obtained to be able to make a reasonable statement about the optical property, for example the chlorophyl content of the plants or the infestation of the leaves with illnesses or pests, in this region. Using the proposed sensor system, a valid measured value can be obtained at leaf inclinations to the beam axis of up to 30°. Depending on the optics of the receiver, the measuring speed, and the advance or travel speed of the sensor system, a value pair can be detected every 2 mm. I.e., a value pair is detected every 2 mm. Therefore, sufficiently many measured values can be recorded so that at least five valid measured values per square meter are provided with sufficiently great probability. However, with such a number of measurements, not only must a corresponding sensor system be provided, but the most simple and rapid method possible must also be used for the analysis, which delivers results within a short time or rapidly discards results which cannot be analyzed, respectively.

In measuring devices which are to carry out very rapid measurements and analyses by means of operational amplifiers, the quotient calculation always causes difficulties. It is therefore proposed that the vegetation indexes be calculated with the aid of the natural logarithm. The quotient calculation of the typical normalized vegetation index (NDVI) is converted into a difference of the natural logarithms. Therefore, not only do advantages result in the technical implementation of the circuit, but rather also larger numeric differences result in the case of leaves having different chlorophyl contents. Smaller differences in chlorophyl content of the leaves can thus be substantially better recognized.

The novel index is only abbreviated with the letters ln NDVI in the scope of this application, based on the NDVI. In the ln NDVI, the difference of natural logarithms of the spectral reflection factors is determined.

According to a fifth aspect of the invention, the signals S of the receivers can also be used instead of the spectral reflection coefficients ρ. Accordingly, a method is provided for analyzing a measurement to determine an optical property of a plant having the steps of detecting a value pair, which has a signal $S_{grün}$ of a first receiver and a signal $S_{rot}$ of a second receiver, and determining a normalized logarithmic vegetation index ln $NDVI_{Blatt}$ by means of the following equation:

$$\ln NDVI_{Blatt} = K \cdot \ln(S_{grün} - S_{rot}) - \ln(S_{rot}),$$

wherein K is a calibration factor, and wherein the value pair is discarded at least if the term $\ln(S_{grün} - S_{rot})$ cannot be determined, and ln $NDVI_{Blatt}$ is calculated if the term $\ln(S_{grün} - S_{rot})$ can be determined. Accordingly, calibration factors $K_1$ to $K_n$ are then required, which specify a device-specific calibration curve, which is dependent, inter alia, on the laser power, the receiver, the optics, and the electronic amplification. The device must be measured or calibrated to ascertain the calibration curve K.

The improved analysis will be clear from the following example. For example, in the case of a leaf having a low chlorophyl content (Chl) of 11 μg Chl/cm$^2$, the following values result: $\rho_{grün} = 0.24$ and $\rho_{rot} = 0.14$. The novel ln NDVI is then calculated to be $-0.336472237$. A leaf having a higher chlorophyl content of 40 μg Chl/cm$^2$ results in $\rho_{grün} = 0.11$ and $\rho_{rot} = 0.06$. The novel ln NDVI is calculated to be $-0.182321557$. The greater sensitivity of the logarithmic index ln NDVI can be recognized from the quotient $(-0.3364/-0.1823)$ of 1.847. Only a quotient of 0.89 would have resulted using the original formula for $$NDVI = \frac{\rho_{grün} - \rho_{rot}}{\rho_{grün} + \rho_{rot}}.$$

Furthermore, through the novel analysis, a simple recognition results as to whether measurement was carried out on a leaf or radiation reflected from the ground was received, for example. In the case of non-green surfaces, the signal of the receiver for red radiation is greater than that of the receiver for green radiation. The difference $\rho_{grün} - \rho_{rot}$ is then negative, and the natural logarithm cannot be calculated. The natural logarithm of a negative number does not exist and therefore results in an error message. This can be used to discard the ground measurements.

In this manner, a plurality of measurement results can be analyzed rapidly.

According to a sixth aspect of the invention, a method for analyzing a measurement to determine an optical property, in particular the chlorophyl content, the infestation of illnesses, fungi, caterpillars, etc., of a plant is proposed, which has the step of detecting a value pair, and determining a parameter $A_Q$ by means of the equation $$A_Q = K_1 \cdot \frac{\rho_{rot}}{\rho_{grün}},$$

wherein $\rho_{grün}$ is the degree of reflection for green light and $\rho_{rot}$ is the degree of reflection for red light. The factor $K_1$ is a component of a calibration curve for linearizing and adapting the scale of a sensor system, which was used for detecting the value pair. The factor $K_1$ is dependent, inter alia, on the laser power, the receiver, the optics, the electronic amplification, and the measuring range. The sensor system must be measured or calibrated to ascertain the calibration curve K.

At a factor $K_1 = 100$, the equation delivers $A_Q = +30$ for green plants with little chlorophyl and $A_Q = +75$ in the case of leaves having a large amount of chlorophyl. An increasing chlorophyl content in the leaves results in an increase of the $A_Q$ value. Therefore, no rethinking by the operator is required. A higher value always indicates a higher chlorophyl content. If green plant parts are not detected using the measuring device, but rather leaves which are colored as a result of illnesses, or ground components, snow residues, or leaf pests, an $A_Q$ value is displayed which is greater than +100. For example, snow residues deliver an $A_Q = +101$, gray mycelia an $A_Q = +110$, brown spots of the leaves an $A_Q = +133$, limestone an $A_Q = +155$, dead pine needles an $A_Q = +176$, and dry sand an $A_Q = +189$.

According to a seventh aspect of the invention, a method is proposed for analyzing a measurement to determine an optical property, in particular the chlorophyl content, the infestation of illnesses, fungi, caterpillars, etc., of a plant, in particular in the case of strongly differing measured values, which has the steps of detecting a value pair, and determining a parameter $A_{ln}$ by means of the equation $$A_{ln} = \frac{K_2}{\ln \rho_{grün} - \ln \rho_{rot}},$$

wherein $\rho_{grün}$ is the degree of reflection for green light and $\rho_{rot}$ is the degree of reflection for red light. Directly upon the determination of the degree of reflection, the natural logarithm (ln) is calculated from the degree of reflection. $K_2$ is a factor for linearizing and adapting the scale of the measuring device. At a factor $K_2 = 50$, the equation delivers an $A_{ln} = +40$ for green plants with little chlorophyl and, in the case of leaves with a large amount of chlorophyl, an $A_{ln} = +180$. An increasing chlorophyl content in the leaves results in an increase of the $A_{ln}$ value, which are all in the positive range. Therefore, no rethinking by the operator is necessary. A higher value always indicates a higher chlorophyl content. If no plants are detected using the measuring device, but rather ground components or snow residues, leaf pests, or leaves which are colored as a result of illnesses, a strongly negative $A_{ln}$ value is displayed, which is <−50. For example, dry sand delivers an $A_{ln} = -78$, dead pine needles an $A_{ln} = -88$, limestone an $A_{ln} = -113$, brown spots of the leaves an $A_{ln} = -173$, gray mycelia an $A_{ln} = -525$, and snow residues an $A_{ln} = -3415$.

A very good differentiation between the detected measured objects is possible through the $A_{in}$ values. In the case of young plants which lie on the ground, the positive measured value of the green leaf can be immediately separated from the negative measured value of the ground. The measured value of the ground is then no longer incorporated in the averaging, as occurs in the known systems, which simultaneously and inseparably detect a large ground surface having small plant fraction and large ground fraction. The class of the healthy green chlorophyl-containing leaves delivers $A_{in}$ values of +40 to +200. The class of the ground, illnesses, and pests delivers negative $A_{in}$ values. A further advantage is the possibility of differentiating between useful plants and foreign plants (weeds). The fraction of the foreign plants in the useful plant stock can be calculated, in that the class of the chlorophyl-containing plants is classified according to the $A_{in}$ values. A further advantage is the possibility of determining the percentage fraction of leaf illnesses or pests in the useful plant stock. If no ground can be detected as a result of the limited measuring cylinder, which does not extend to the ground, the leaf illnesses and pests are clearly differentiable from the healthy leaves, because healthy useful plants always deliver positive $A_{in}$ values and leaf illnesses or pests always deliver negative $A_{in}$ values.

In the sensor system according to the invention, it can further be provided in one refinement that a second receiver is provided, wherein the second receiver is aligned along a fourth beam axis in such a manner that a second measuring cylinder, which extends along the fourth beam axis, and the first measuring cylinder and the target cylinders at least partially overlap one another in the measuring space, and the first beam axis and the second beam axis respectively enclose an angle with the fourth beam axis.

In this manner, it is possible to respectively provide a receiver for each wavelength range, which is accordingly sensitized for this wavelength range. Furthermore, both receivers can be operated continuously. In the case of only one receiver, it must record the reflected radiation of the first light source and the second light source offset in time, for example. By means of the continuous recording of respectively one receiver, more reliable measurement results can be achieved.

In particular, it can be provided that the first light source and the second light source are arranged in a first housing, and the at least one first receiver is arranged in a second housing. For example, if two receivers are provided, the first and the second receivers are accordingly arranged in a second housing.

To carry out the reflection method according to the invention, light source and receiver are to be provided in separate housings or in sections of the same housing which are optically separated from one another, which is also to be understood as included by "separate housing" in the meaning of the invention. The ratio of the amplitude of the transmitted signal to the received signal is approximately in a size ratio of 1,000,000:1. In the case of an arrangement of light sources and receivers in the same housing or without optical separation from one another, the received signal would necessarily be superimposed with reflections of the transmitted signal or the light source, respectively, within the housing.

In particular, it can be provided that the first light source emits light in a first wavelength range and the second light source emits light in a second wavelength range.

As was already stated at the beginning, it is possible in this manner to detect a reference value and thus to infer the absolute reflection coefficients, independently of whether the degree of reflection is influenced by a leaf inclination.

Furthermore, it can be provided that each receiver has an optical bandpass filter, which is transmissive for light of the first wavelength range and/or of the second wavelength range.

A substantial interfering influence of the reflection method is the solar radiation, for example the sunlight reflected from the plant, which is also detected by the at least one receiver.

The signal-to-noise ratio can thus be improved by the bandpass filters, in that only light in the corresponding wavelength range is let through.

In particular, it can be provided that the first wavelength range is a wavelength range of green light and the second wavelength range is a wavelength range of red light. However, other wavelength ranges, for example in the near infrared range, can also be used.

It was already explained at the beginning that green light is reflected particularly well from chlorophyl-containing plants and therefore a strongly chlorophyl-dependent reflection coefficient prevails in the green wavelength range. In contrast thereto, the reflection coefficient in the red wavelength range is not as strongly chlorophyl-dependent and can be used as the reference value.

In the scope of the present invention, the wavelength ranges are assigned to the spectral colors approximately as follows: violet: 380 to 420 nm, blue: 420 to 490 nm, green: 490 to 575 nm, yellow: 575 to 585 nm, orange: 585 to 650 nm, red: 650 to 780 nm, and infrared greater than 780 nm.

The most favorable wavelength ranges for detecting the chlorophyl content are at 555 nm and at approximately 650 to 690 nm. In one refinement of the invention, it can be provided that the light sources are lasers having an average power of approximately 0.2 mW to approximately 4.5 mW. The powers of the lasers are therefore in a low range of the eye safety for commercially used lasers. The corresponding limiting values can be inferred from the norm DIN EN 60825-1. The laser wavelength cannot be selected arbitrarily; it is specified by the physical properties of the stimulated emission. Typical laser wavelengths are at respectively approximately 515 nm, 532 nm, 635 nm, 650 nm, 670 nm, 780 nm, 808 nm, and 905 nm. For example, a green laser having approximately 532 nm wavelength and a red laser having approximately 670 nm wavelength can be used.

Furthermore, it can be provided in combination with the remaining refinements of the invention that the light emitted by the first light source and by the second light source is modulated with a constant modulation frequency and the at least one first receiver preferably detects the modulation frequency or is tuned thereto, respectively. In particular, it can be provided that the light emitted by the first light source and by the second light source is modulated pulsed in a rectangular or sinusoidal manner at constant frequency and the at least one first receiver only analyzes electrical signals within a frequency bandwidth in which the pulse frequency of the light source lies.

It can also be provided that the first light source and the second light source each emit light pulsed in a constant frequency, wherein the frequencies are different from one another, wherein the at least one first receiver analyzes signals which have the frequency. Two receivers can be provided, wherein a first receiver is tuned to the frequency of the first light source and a second receiver is tuned to the frequency of the second light source or analyzes it, respectively. If only one receiver is provided, it is tuned to both frequencies or analyzes them, respectively.

The light sources or lasers are thus activated using an electronic assembly in such a manner that they output alternating radiation, i.e., pulsed radiation, at a specific clock frequency. The alternating radiation is radiated from the light source onto the leaf and is reflected from the incidence surface of the leaf. The light beams do not change their clock frequency through the reflection, but rather only their amplitude, which becomes smaller. The alternating radiation reflected from the leaf or the plant, respectively, decisively differs from a constant-light interfering radiation, for example from the radiation of the sun or from headlight lamps. The alternating radiation of the light source which reaches one of the receivers generates an AC voltage. For this purpose, receivers having downstream AC voltage amplifiers are used, which only analyze signals in a narrow frequency bandwidth, in which the frequency of the pulsed light or laser radiation also lies. The constant-light interfering radiation of the sun generates a DC voltage in the receiver. In a downstream circuit, only the AC voltage is processed further and the DC voltage is blocked.

In addition, it can be provided in one refinement that the first beam axis and the second beam axis are not congruent. Furthermore, in the case in which two receivers are provided, it can be provided that the third beam axis and the fourth beam axis are not congruent.

The receiver delivers a measuring signal having high amplitude only if a target cylinder and also the associated measuring cylinder overlap one another. It can be provided that a threshold value or a measured value range, respectively, is stored and the chlorophyl content of a leaf or a plant is only determined if the receivers deliver signals which are greater than the predefined threshold value or are within the measured value range, respectively. This will only be the case if the target cylinders largely overlap one another. This is the case in the so-called measuring area. Since a certain depth extension or three-dimensional extension of the measuring area exists, of course, this could also be designated as the "measuring space", which has a cylinder-like form. Therefore, the term measuring space is used hereafter in the present case.

In particular, it can be provided that a fastening of the first light source and of the second light source and of the at least one first receiver is provided such that the angles between the beam axes of the light sources and the beam axis of the at least one receiver and a distance between the light sources and the at least one receiver can be adjusted.

In this manner, the measuring space of the sensor system or the location of the measuring space is particularly easily adjustable. The measuring space can thus be adjusted to the leaf height of the plants to be measured. Objects which are located outside the measuring space, i.e. in front of or behind it, do not deliver any reflection signals which are greater than the threshold value or are within the measured value range, respectively. In this manner, the ground reflections or reflections from other growth or random excessively large signals of taller plants can already be electronically suppressed.

This is advantageous in particular in stationary sensor systems, which are installed on farm vehicles, for example. These sensor systems measure a large-area plant growth, which continuously has the same development stage and therefore approximately the same leaf height.

In sensor systems which are used as handheld devices, the distances to the plant parts to be measured vary during the measurement. However, in these handheld devices, measured values which do not originate from reflections from plants can be discarded, for example, via the analysis method provided according to the invention by means of the ln NDVI or the $A_Q$ or $A_{ln}$ value.

If handheld devices are used, it is favorable to not only display the measured value on a scale, but rather also signal it acoustically. Therefore, the sensor system according to the invention can have a signal generator, which is acoustic in particular. In one of the methods according to the invention, it can be provided that an analysis result is transmitted to a user by means of a signal generator, in particular acoustically. The operator is therefore freed from observing the measuring point on the leaf and the scale simultaneously. The pitch range for chlorophyl-containing leaves lies in a mean tone range from 200 Hz to 400 Hz, wherein the pitch rises when the chlorophyl content rises. If ground is detected, a lower tone of 75 Hz to 150 Hz occurs. In the event of pest infestation or leaf illnesses, a higher tone of 500 Hz to 600 Hz is emitted.

In one refinement of the invention, it can further be provided that the target cylinder of the first light source and the target cylinder of the second light source in the measuring space each have a diameter of approximately 1 mm to approximately 6 mm, wherein the measuring cylinder of the at least one receiver in the measuring space has a diameter of approximately 8 mm.

The diameter of the region in which the sensor system determines a chlorophyl content is therefore very small in relation to the sensors and methods known from the prior art. A region of multiple square meters is not scanned and an average is not calculated over all detected objects such as leaf mass, stalks, flowers, soil, rocks, etc., but rather essentially a punctual measurement is carried out at an adjustable measuring distance to the sensor system and within an adjustable measuring space. In operation, several hundred punctual measurements per second can then be carried out, so that a sufficient number of valid measurement results of green leaves per area of the field which is covered is achieved with nearly certain probability.

In a refinement of the methods for analyzing a measurement to determine an optical property of a plant, it can further be provided that the value pair is also discarded if one or both of the signals or one or both of the reflection coefficients, respectively, leave a predetermined threshold range, in particular are greater than or less than a predetermined threshold value.

The proposed sensor system and the proposed methods therefore substantially differ from the previously proposed measuring methods, since a changeover is made from a large-area measuring procedure to a multiplicity of small-area or punctual measuring procedures, and therefore in particular the advantage is achieved of being able to determine an optical property within a leaf area.

It is obvious that the abovementioned features and the features still to be explained hereafter are usable not only in the respectively specified combination but rather also in other combinations or alone, without leaving the scope of the present invention.

BRIEF DESCRIPTION OF THE DRAWINGS

Exemplary embodiments of the invention are illustrated in the drawing and will be explained in greater detail in the following description. In the figures.

DETAILED DESCRIPTION OF THE INVENTION

Figure 1:
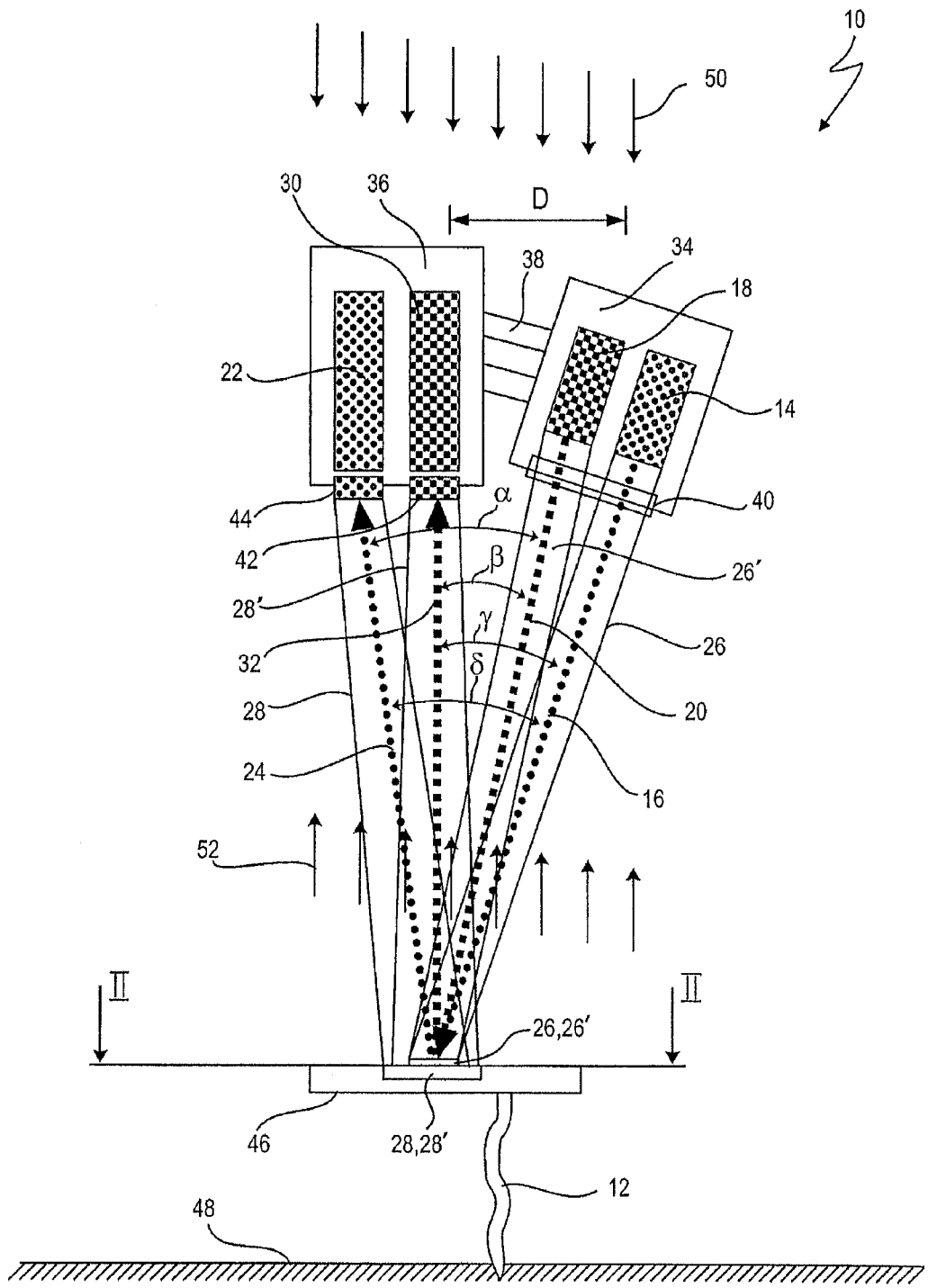
FIG. 1 shows a schematic view of an embodiment of a sensor system.

FIG. 1 shows a sensor system 10 according to an embodiment of the invention. The sensor system 10 is used to determine the chlorophyl content of a plant 12 by means of a reflection measurement.

The sensor system 10 has a first light source 14, which emits light along a first beam axis 16, and a second light source 18, which emits light along a second beam axis 20. The light sources 14, 18 are embodied as lasers, wherein, for example, the first light source 14 emits light having a wavelength of approximately 532 nm, i.e., in the green wavelength range, and the second light source 18 emits light in a wavelength of approximately 670 nm, i.e., in a red wavelength range.

Furthermore, the sensor system 10 has a first receiver 22, which is aligned along a third beam axis 24. A target cylinder 26, 26', in which the beam bundle of the corresponding laser extends, respectively extends along the first beam axis 16 and the second beam axis 20. The target cylinders 26, 26' each have a diameter of, for example, approximately 2 mm. "Essentially cylindrical" is understood to mean that the target cylinder 26 has no widening or only very slight widening. Very slight widening can be in the range of 2 mrad, for example. This also applies for the target cylinder 26'.

A measuring cylinder 28, i.e., the spatial region with which the receiver is aligned, extends along the third beam axis 24 of the first receiver 22.

The first receiver 22 is provided for the purpose of receiving light in a green wavelength range, i.e., the light of the first light source 14.

Furthermore, a second receiver 30 is provided, which is aligned along a fourth beam axis 32. A further measuring cylinder 28' of the second receiver 30 extends along the fourth beam axis 32.

The first light source 14 and the second light source 18 are provided in a first housing 34. The first receiver 22 and the second receiver 30 are provided in a second housing 36.

The first housing 34 and the second housing 36 are connected using a fastening mechanism 38.

By means of the fastening mechanism 38, the first housing 34 and the second housing 36 can be adjusted both in their distance D relative to one another and also in their angles of inclination. With the aid of the fastening mechanism 38, an angle α between the second beam axis 20 and the third beam axis 24, an angle β between the second beam axis 20 and the fourth beam axis 32, an angle γ between the first beam axis 16 and the fourth beam axis 32, and an angle δ between the first beam axis 16 and the third beam axis 24 may thus also be adjusted. In this manner, it is possible, as will be described in greater detail hereafter, to adjust the measuring space of the sensor system 10. Of course, the fastening mechanism 38 can also be designed such that the distance D is fixed and only the angles α, β, γ, and δ may be adjusted. The receivers 22, 30 and the light sources 14, 18 can also each be housed separately in a separate housing, so that the angles α, β, γ, and δ are adjustable separately and independently of one another.

Furthermore, a second optical bandpass filter 42 is provided upstream from the second receiver 30. This bandpass filter 42 is adjusted such that it is primarily transmissive for light beams of the wavelength range which is emitted by the second light source 18, i.e., red radiation in a wavelength range of approximately 670 nm in the present case. Furthermore, a first optical bandpass filter 44 is provided upstream from the first receiver 22. It is only transmissive for green radiation of approximately 532 nm, so that it primarily lets through the radiation of the first light source 14.

The radiation emitted from the first light source 14 and from the second light source 18 is reflected from a leaf 46 of the plant 12. The leaf 46 is located above ground 48. The radiation reflected from the leaf 46 then enters the first receiver 22 and the second receiver 30.

Of course, solar radiation 50 also exists, which is also reflected from the leaf 46, so that reflected solar radiation 52 can also enter the first receiver 22 and the second receiver 30.

However, substantial power fractions of this interfering radiation or reflected solar radiation 52, respectively, can already be suppressed by the bandpass filters 42 and 44, inter alia. Only the red light of the reflected solar radiation 52 and of the red light source 18 still passes through the red bandpass filter 42. Only the green light of the reflected solar radiation 52 and of the green light source 14 still passes through the green bandpass filter 44.

A further removal of diverse interference sources can be achieved in that the radiation of the first light source 14 and of the second light source 18 is delivered, for example, in pulsed form or as sinusoidal alternating radiation. For example, it can be provided that the first light source 14 and the second light source 18 emit pulsed laser radiation at a specific frequency. This alternating radiation which then reaches the receivers 22, 30 generates an AC voltage in the receivers 22, 30, which can be photodiodes, for example. The constant-light interfering radiation 52 generates a DC voltage in the receivers 22, 30. By means of a suitable downstream circuit, only the AC voltage is further processed and the DC voltage is blocked.

With the aid of these measures, the electrical interfering voltages which are caused by solar radiation and other constant-light radiation in the receivers 22, 30 can be substantially suppressed by means of the sensor system according to the invention.

Figure 2:
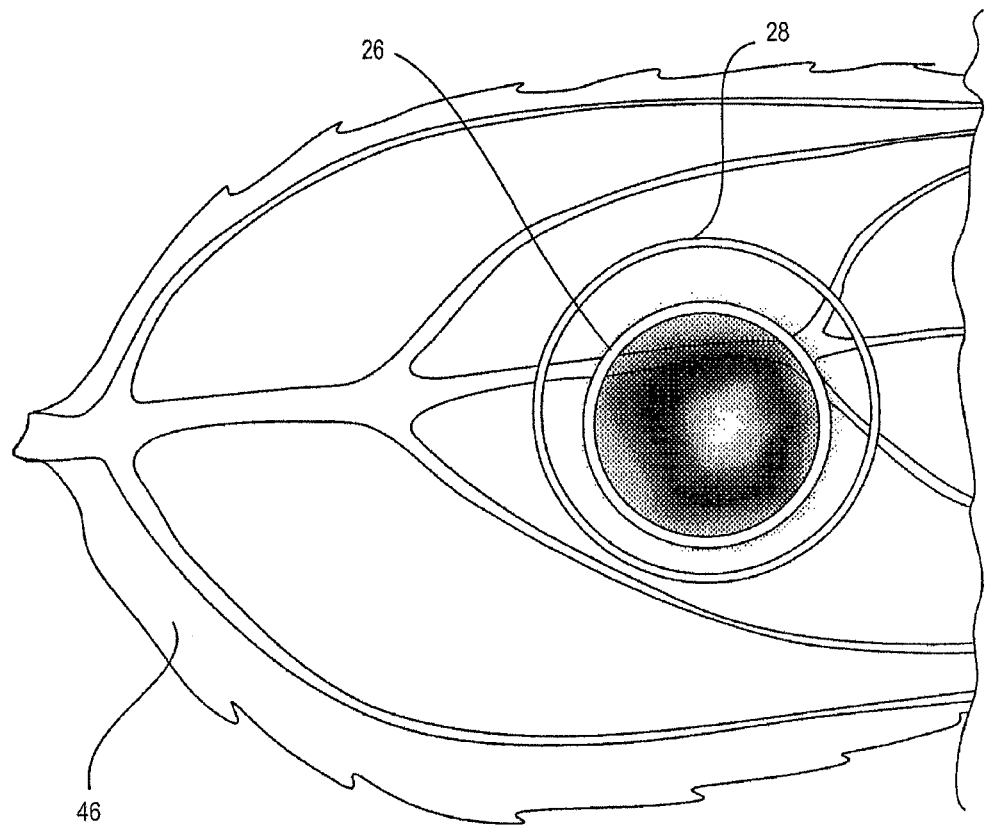
FIG. 2 shows a schematic top view along a line II-II in FIG. 1.

FIG. 2 shows a schematic top view along a line II-II in FIG. 1.

The top view of the leaf 46 is shown. An outline of the target cylinder 26 and an outline of the measuring cylinder 28 are shown therein. As may be recognized, the laser beams of the first light source 14 and of the second light source 18 are located inside the target cylinder 26. The target cylinders 26, 26' overlap one another completely in the illustrated top view, i.e., they are congruent. Fundamentally, it can be provided that the first light source 14 and the second light source 18 can also be inclined relative to one another within the first housing 34, in order to adjust the first beam axis 16 and the second beam axis 20 relative to one another. In this manner, the plane in which the target cylinders 26, 26' are congruent can be adjusted. This is also true for the first receiver 22 and the second receiver 30, which can also be arranged so that they are adjustable relative to one another within the second housing 36.

In the illustrated view in FIG. 2, the measuring cylinders 28, 28' are also congruent in the sectional view. The illustrated view therefore represents an optimal state, which is only achieved at a specific height, as explained hereafter.

If the target cylinders 26, 26' are located completely in the measuring cylinders 28, 28', the power of the reflected light is sufficiently high that it clearly exceeds a certain threshold value, which is predefined. In this case, an analysis of the measurement results occurs. If the target cylinders 26, 26' and the measuring cylinders 28, 28' only overlap to a small extent or not at all, the power falls below this threshold value, and no analysis of the measurement results occurs. This is the case in particular, as explained hereafter, if light is reflected from objects which are located excessively high or excessively low.

Figure 3:
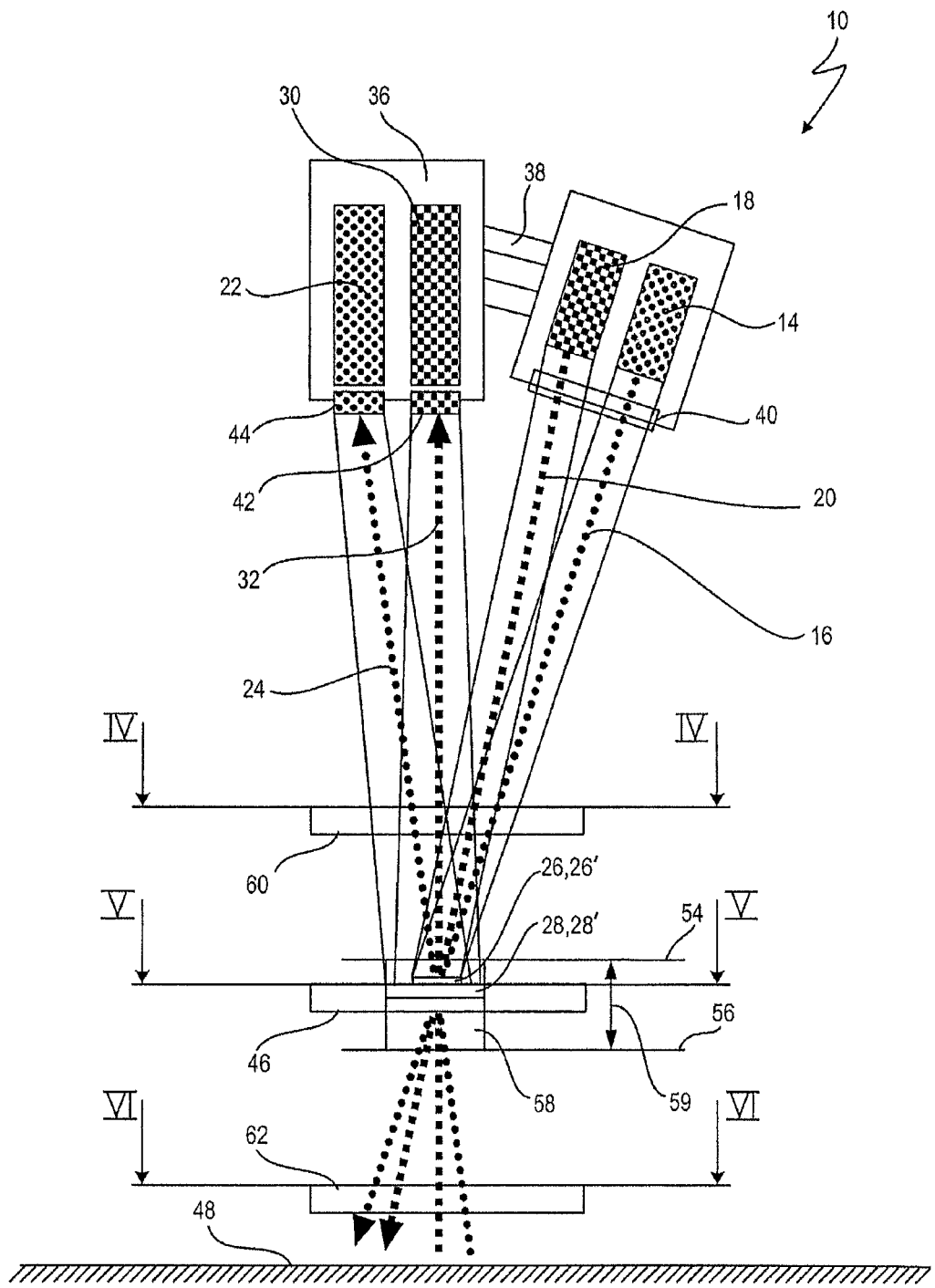
FIG. 3 shows the sensor system in FIG. 1 with illustration of valid and invalid measuring regions.

FIG. 3 shows the embodiment of the sensor system in FIG. 1. In addition, an upper usable measuring plane 54 and a lower usable measuring plane 56 are shown. If the leaf 46 is located between the usable measuring planes 54, 56, the target cylinders 26, 26' and measuring cylinders 28, 28' overlap one another sufficiently that the threshold value defined in the present case is exceeded and an analysis of the measurement results is performed. The measuring space 58 having the usable height layer 59 results therefrom. The measuring space 58 therefore has a certain extension in the vertical direction.

Thus, only an analysis of the reflected light of objects which are located within the measuring space 58 occurs. In this manner, for example, in a sensor system which is attached to a farm vehicle or a farm machine, the height layer 59, in which the leaves 46 to be measured are located, may be adjusted knowing the plant growth to be measured. During the travel or during the fertilizing procedure, respectively, the chlorophyl content of the leaves in this measuring space 58 can then be determined and the nitrogen content of the plants 12 can be concluded. It is thus possible to determine the fertilizer quantity to be applied during travel in real time.

Figure 4:
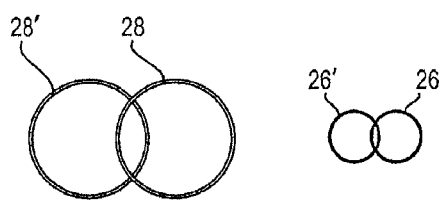
FIG. 4 shows a schematic top view along a line IV-IV in FIG. 3.

If an object moves in a measuring space 60 located excessively high into the region of the sensor 10, the arrangement shown in FIG. 4 results.

FIG. 4 shows the top view of a plane IV-IV in FIG. 3, which indicates the case of a leaf 46 located excessively high. The target cylinders 26, 26' and the measuring cylinders 28, 28' are not coincident. Radiation emitted from the first light source 14 and from the second light source 18 cannot be detected by the receivers 22 and 30. The radiation power of the alternating radiation which is received in the first receiver 22 and the second receiver 30 is therefore extremely low or is even equal to zero. In any case, the radiation power is less than the predefined threshold value. An analysis therefore does not occur.

Figure 5:
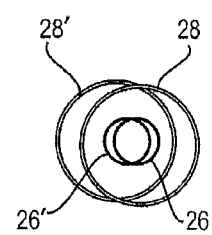
FIG. 5 shows a schematic top view along a line V-V in FIG. 3.

FIG. 5 shows a top view of a plane V-V in FIG. 3 having a leaf 46 in the measuring height 59 and within the measuring space 58. The measuring cylinders 28, 28' completely overlap the target cylinders 26, 26'.

Figure 6:
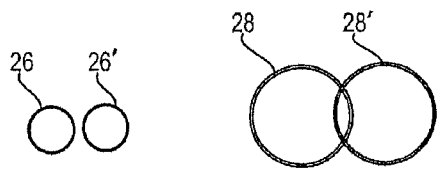
FIG. 6 shows a schematic top view along a line VI-VI in FIG. 3.

FIG. 6 shows a top view of a plane VI-VI in FIG. 3 having a leaf 46 in a height layer 62 located excessively low. No analysis of a measurement result also occurs here because of a lack of an overlap of the target cylinders 26, 26' and the measuring cylinders 28, 28'.

In this manner it is possible to eliminate measured values from undesired height layers in the case of stationary sensor systems, which are attached to farm vehicles, for example.

If the sensor system 10 is used as a portable handheld device, in which the distance to the plants to be measured continuously varies, the target cylinders 26, 26' and the measuring cylinders 28, 28' are to be adjusted such that the angles, for example through a shorter length of the fastening 38, decrease the distance between the two housings 34 and 36 and therefore the angles α, β, γ, δ are decreased. In the case of a handheld device, an optimum measuring plane is recognizable very well by the human eye, because the green target cylinder 26 and the red target cylinder 26' overlap in a manner which is very well visible, since they form a bright yellow spot as a result of the color mixture of green and red. Thus, as long as the two target cylinders 26 and 26' do not overlap at least partially in the form of a bright yellow spot, no measured values can be recorded in the case of the handheld device.

In order that the user of the handheld device does not have to concentrate simultaneously on the correct measuring distance and the reading off of the measured values, for example, it can be provided that in the case of a measurement of the chlorophyl content, upon reaching a measured value which corresponds to the minimum concentration of chlorophyl, a short tone of moderate pitch is sounded. With increasing chlorophyl content, the pitch increases; with decreasing chlorophyl content, the pitch decreases. Upon detection of a brown ground surface or black fungus infestation of the leaves 46, a lower tone is sounded. If many measured values at identical chlorophyl content are output within a short time, a rapid tone sequence of equal pitch sounds. The tone sequence becomes slower if few measured values are output. If no reasonable measured value is output, a deep continuous tone occurs to acoustically indicate the measurement readiness of the device. If the sensor system 10 having an acoustic measured value output or an acoustic signal generator, respectively, is used in a stationary manner on a farm vehicle, the driver can concentrate better on the driving route and does not have to read off the measured values from a display screen simultaneously.

Figure 7:
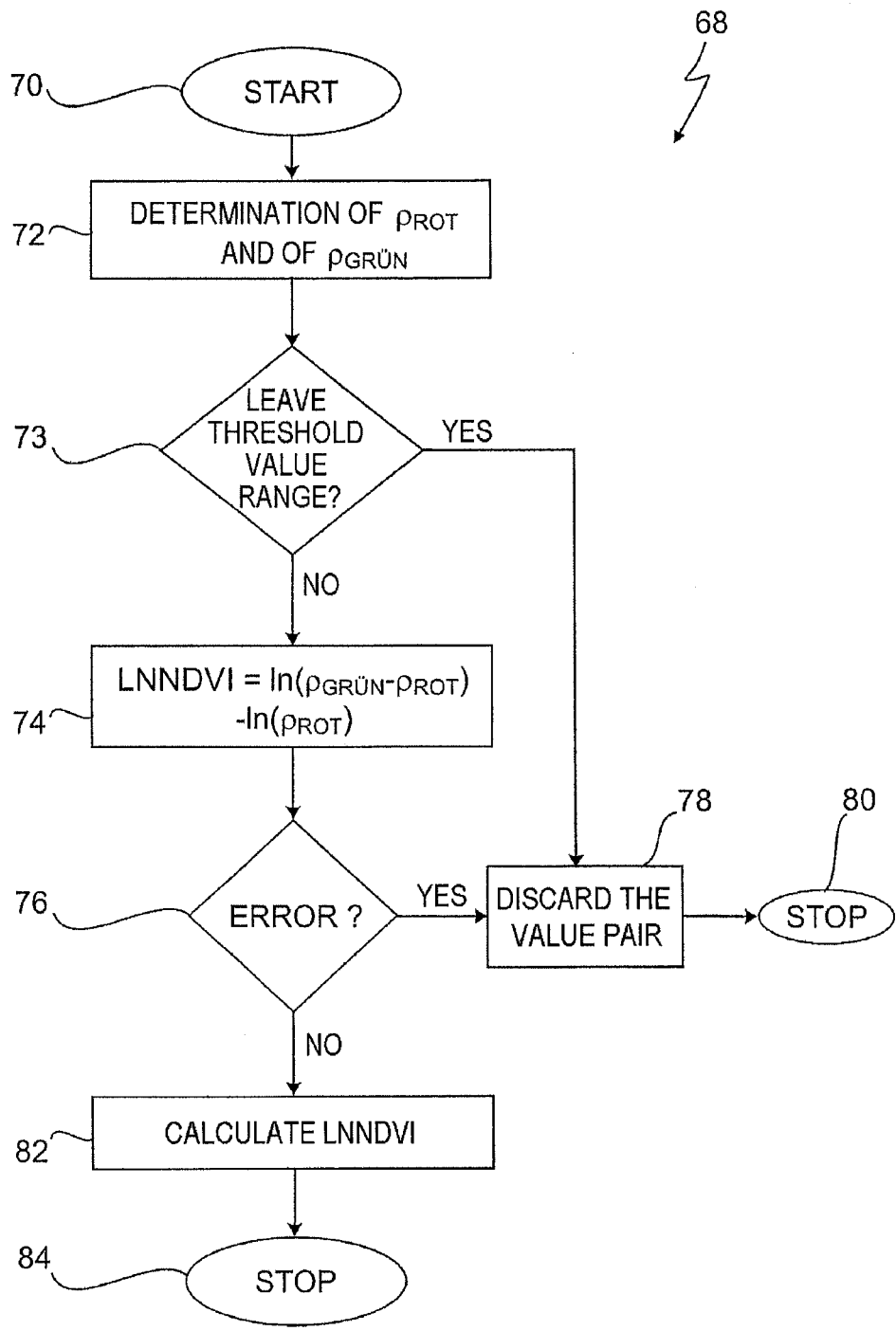
FIG. 7 shows a schematic flow chart of a method for analyzing a measurement to determine an optical property of a plant.

FIG. 7 shows a schematic flow chart of a method 68 for analyzing measurement results during the determination of an optical property of a plant, for example the measurement of the chlorophyl content of a plant 12, the determination of illnesses, or the infestation of the leaf 46 with pests.

The method 68 begins with a starting step 70. In a step 72, firstly a reflection coefficient $\rho_{rot}$ and a reflection coefficient $\rho_{grün}$ are determined in the first receiver 22 and in the second receiver 30. The reflection coefficients $\rho_{rot}$ and $\rho_{grün}$ merely stand as examples for reflection coefficients which were achieved at various wavelengths, wherein one of the wavelengths has a strongly chlorophyl-dependent reflection coefficient and the other wavelength has a strongly chlorophyl-independent reflection coefficient. These do not necessarily actually have to be a red and a green wavelength range, but this is preferred.

Optionally, a check can then occur in a step 73 as to whether the determined reflection coefficients $\rho_{rot}$ and $\rho_{grün}$ are within a predetermined threshold value range. Very glossy, inclined leaves 46 reflect an unnaturally large amount of light from the light sources 14 and 18 to the receivers 22 and 30, so that a predetermined upper limiting or threshold value is exceeded during the determination of the reflection coefficients. On the other hand, strongly inclined, matte hairy leaves 46 reflect little light, so that a predetermined lower threshold value is undershot during the determination of the reflection coefficients. A lower threshold value can also be undershot in the event of only partial overlap of the measuring cylinders 28, 28' and target cylinders 26, 26'. It is accordingly then provided that in the event of exceeding the upper threshold value or in the event of undershooting the lower threshold value, the value pair is discarded in a step 78 and the method begins again at step 70. Otherwise, the method continues with a step 74.

Subsequently, in step 74, the ln NDVI, i.e., the normalized logarithmic vegetation index, is determined.

If the reflected light radiation originates from a leaf 46, the reflection coefficient $\rho_{grün}$ is greater than the reflection coefficient $\rho_{rot}$. As a result, the term $\ln(\rho_{grün}-\rho_{rot})$ can be determined, since the difference is greater than zero. If the reflection coefficient $\rho_{grün}$ is less than the reflection coefficient $\rho_{rot}$, because the reflected light radiation originates from the ground 48, the difference is negative and the term $\ln(\rho_{grün}-\rho_{rot})$ cannot be determined.

As a result, an error is then determined. Therefore, in a step 76, it is queried whether or not an error exists. If an error exists, the measured value pair is discarded in a step 78, and the analysis of the value pair ends in a step 80. The method then begins step 70 again with the next value pair.

If no error exists, in a step 82, the ln NDVI is calculated and relayed for further analysis, i.e., to determine the chlorophyl or nitrogen content, respectively, of the plant 12.

The method 68 ends in a step 84 and begins again if necessary in step 70 with the next value pair.

The proposed method 68 therefore provides, because of the determination of the ln NDVI, a simple method for discarding reflections from the ground 48. In addition, no divisions are to be performed, so that the calculation can be carried out rapidly by means of simple operational amplifiers. In this manner, it is possible to analyze the several hundred value pairs which are detected per second in real time and to calculate the nitrogen content of the plants 12 to be measured in real time.

Figure 8:
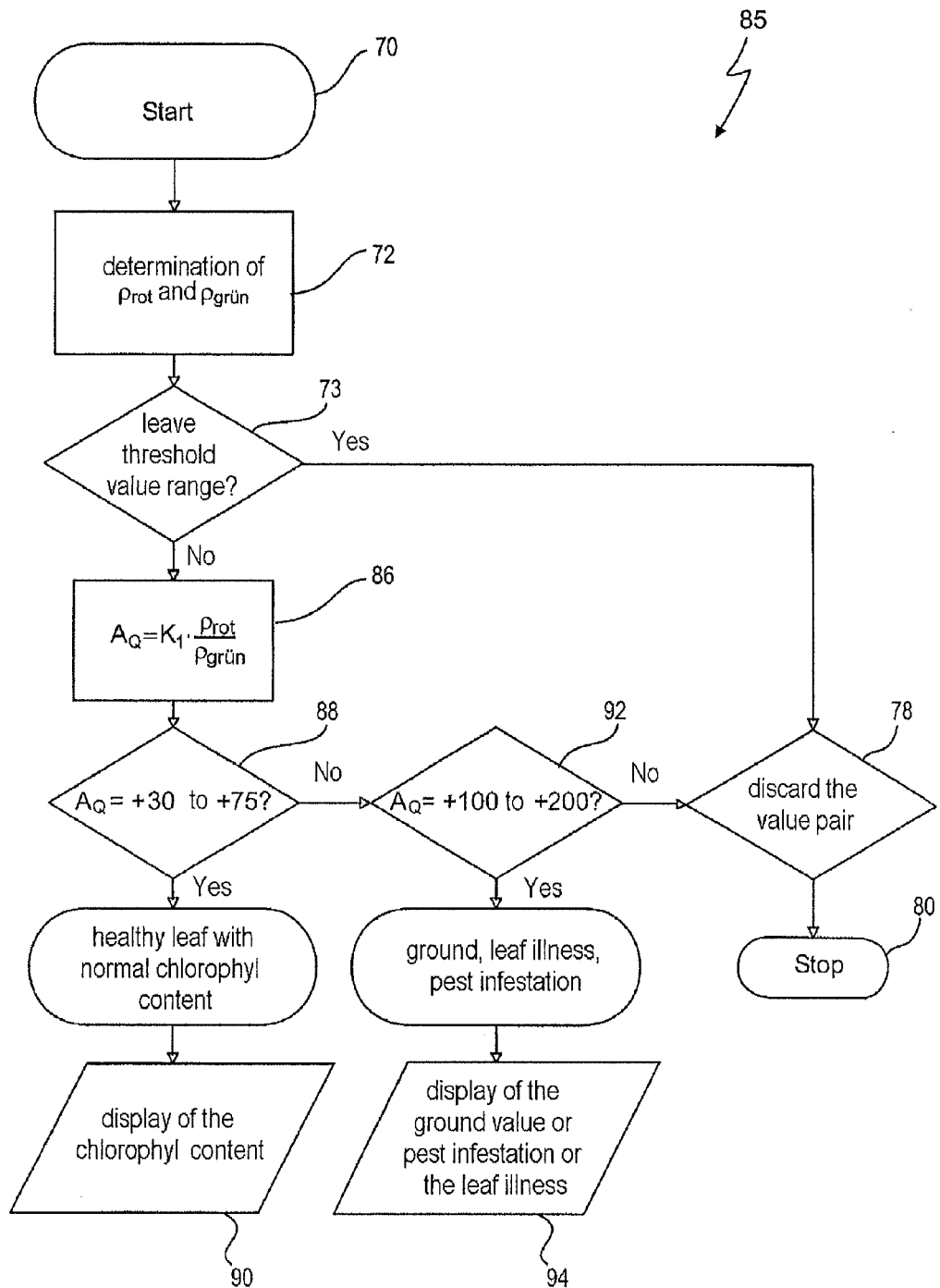
FIG. 8 shows a schematic flow chart of a further method for analyzing a measurement to determine an optical property of a plant.

FIG. 8 shows a schematic flow chart of a further method 85 for analyzing measurement results during the determination of an optical property of a plant 12, for example the measurement of the chlorophyl content of a plant 12, the determination of illnesses, or the infestation of the leaf 46 with pests. Identical reference numerals identify method steps which correspond to those of the method 68 and are not described again hereafter. Only the differences will be discussed.

In a step 86, a parameter $A_Q$ having the constant $K_1=100$ is determined. For green plants having low chlorophyl content, values around +30 result, which rise in the case of leaves having high chlorophyl content to values up to +75. A corresponding query is performed in a step 88 and is output if necessary in a step 90. In contrast, rocks, sand, and soil also deliver positive $A_Q$ values. However, they are in the range of +100 to +200. As a result, values of >100 would not come from green plants, but rather from brown leaf spots, fungi, ground, etc. A safety interval of the numbers exists between <75 (leaf with a large amount of chlorophyl) and >101 (wet snow, rocks, soil, etc.). A corresponding query occurs in a step 92 and is output if necessary in a step 94. The output in steps 90 and 94 can be performed on a display, cumulatively, or alternatively also acoustically.

To detect the quantity of foreign plants (weeds) in a useful stock, the $A_Q$ value in the range from +30 to +75 can be used. The foreign plants are in the minority and typically have deviations from the positive $A_Q$ value range of the healthy green useful plants.

Figure 9:
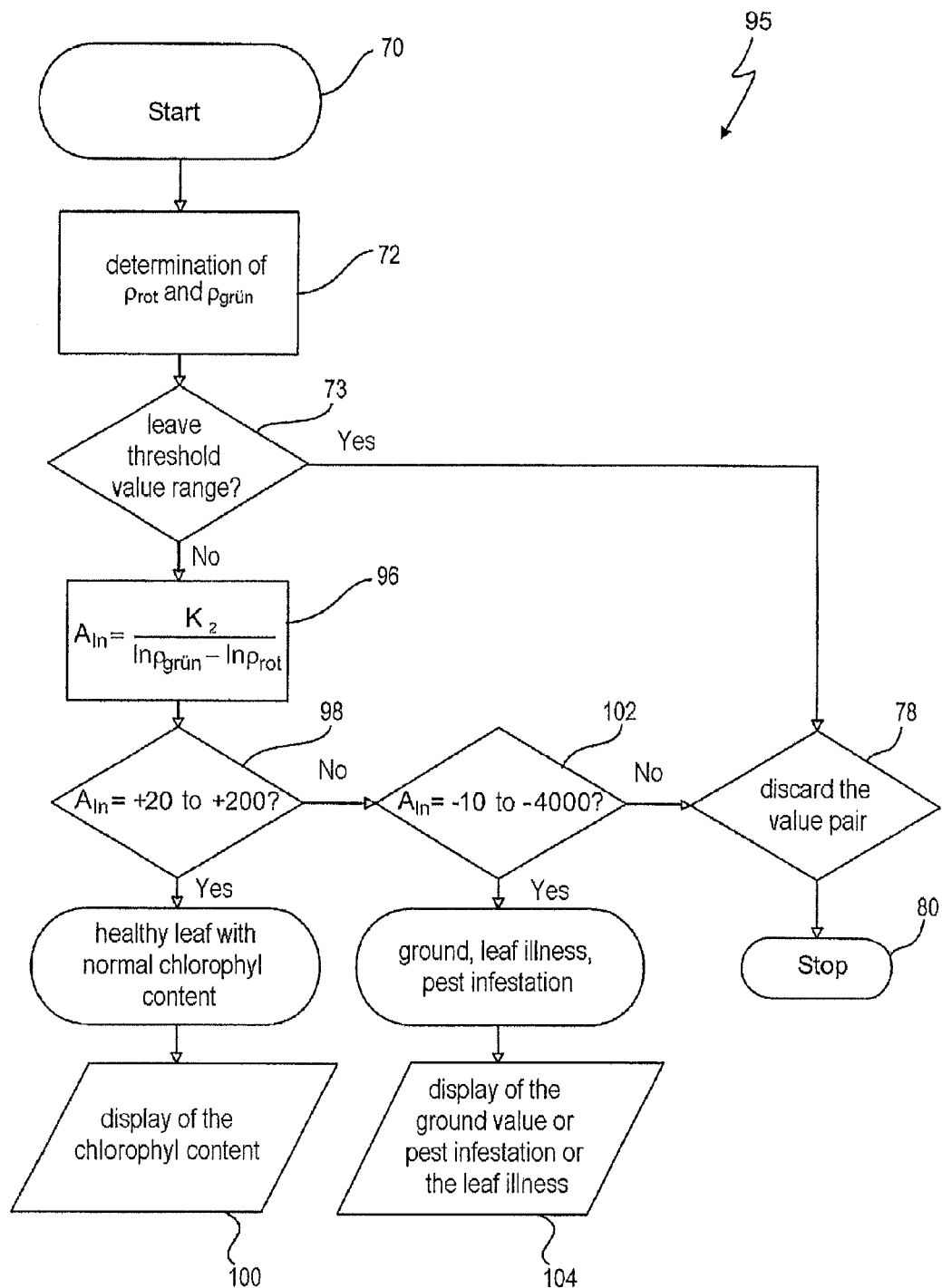
FIG. 9 shows a schematic flow chart of still a further method for analyzing a measurement to determine an optical property of a plant.

FIG. 9 shows a schematic flow chart of a further method 95 for analyzing measurement results during the determination of an optical property of a plant 12, for example the measurement of the chlorophyl content of a plant 12, the determination of illnesses, or the infestation of the leaf 46 with pests. Identical reference numerals identify method steps which correspond to those of the methods 68 and 85 and are not described again hereafter. Only the differences will be discussed.

In a step 96, a parameter $A_{ln}$ having the constant $K_2=50$ is determined. For green plants having a low chlorophyl content, positive values around +40 result, which increase in the case of leaves having a high chlorophyl content to values up to +180. A corresponding query occurs in a step 98 and is output if necessary in a step 100. Natural materials such as rocks, soil, and sand result in negative values of −50 to −500 and can therefore be differentiated very well from green leaves. Wet snow delivers $A_{ln}$ values of approximately −3415. A corresponding query occurs in a step 102 and is output if necessary in a step 104. The output in steps 100 and 104 can be performed on a display, cumulatively, or alternatively also acoustically.

To detect the quantity of foreign plants (weeds) in a useful stock, the $A_{ln}$ value in the range from +30 to +170 can be used. The foreign plants are in the minority and typically have deviations from the positive $A_{ln}$ value range of the healthy green useful plants.

What is claimed is:

1. A sensor system for determining an optical property of a plant by means of a reflection measurement, having a first light source, which emits light along a first beam axis, and a second light source, which emits light along a second beam axis, and at least one first receiver, which is aligned along a third beam axis, to detect light reflected from the plant, wherein the first light source, the second light source, and the at least one first receiver are arranged relative to one another in such a manner that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle with the third beam axis, wherein the first light source emits light in a first wavelength range and the second light source emits light in a second wavelength range, wherein the first wavelength range is a wavelength range of green light, wherein the second wavelength range is a wavelength range of red light, wherein the first light source and the second light source are arranged in a first housing, and the at least one first receiver is arranged in a second housing separate from said first housing, and wherein a fastening of the first light source and of the second light source and of the at least one first receiver is provided such that the angles between the beam axes of the light sources and the beam axis of the at least one first receiver and a distance between the light sources and the at least one receiver can be adjusted.

2. A sensor system for determining an optical property of a plant by means of a reflection measurement, having a first light source, which emits light along a first beam axis, and a second light source, which emits light along a second beam axis, and at least one first receiver, which is aligned along a third beam axis, to detect light reflected from the plant, wherein the first light source, the second light source, and the at least one first receiver are arranged relative to one another in such a manner that a target cylinder of the first light source extending along the first beam axis, a target cylinder of the second light source extending along the second beam axis, and a first measuring cylinder, which extends along the third beam axis, at least partially overlap one another in a measuring space, and the first beam axis and the second beam axis respectively enclose an angle with the third beam axis, wherein the target cylinder of the first light source and the target cylinder of the second light source in the measuring space each have a diameter of approximately 1 mm to approximately 6 mm, wherein the measuring cylinder of the at least one receiver in the measuring space has a diameter of approximately 8 mm.

3. The sensor system as claimed in claim 2, wherein a second receiver is provided, wherein the second receiver is aligned along a fourth beam axis in such a manner that a second measuring cylinder, which extends along the fourth beam axis, and the first measuring cylinder and the target cylinders at least partially overlap one another in the measuring space, and the first beam axis and the second beam axis respectively enclose an angle with the fourth beam axis.

4. The sensor system as claimed in claim 2, wherein the first light source and the second light source are arranged in a first housing, and the at least one first receiver is arranged in a second housing.

5. The sensor system as claimed in claim 2, wherein the first light source emits light in a first wavelength range and the second light source emits light in a second wavelength range.

6. The sensor system as claimed in claim 5, wherein each receiver has an optical bandpass filter, which is transmissive for light of the first wavelength range and/or of the second wavelength range.

7. The sensor system as claimed in claim 5, wherein the first wavelength range is a wavelength range of green light and the second wavelength range is a wavelength range of red light.

8. The sensor system as claimed in claim 2, wherein the light emitted by the first light source and by the second light source is modulated with a constant modulation frequency and the at least one first receiver detects the modulation frequency.

9. The sensor system as claimed in claim 2, wherein the first light source and the second light source each emit light pulsed in a constant frequency, wherein the frequencies are different from one another, wherein the at least one first receiver analyzes signals which have one of the frequencies.

10. The sensor system as claimed in claim 2, wherein the first beam axis and the second beam axis are not congruent.

11. The sensor system as claimed in claim 2, wherein the first beam axis and the second beam axis are congruent.

12. The sensor system as claimed in claim 3, wherein the third beam axis and the fourth beam axis are not congruent.

13. The sensor system as claimed in claim 2, wherein a fastening of the first light source and of the second light source and of the at least one first receiver is provided such that the angles between the beam axes of the light sources and the beam axis of the at least one receiver and a distance between the light sources and the at least one receiver can be adjusted.

14. The sensor system as claimed in claim 2, wherein the sensor system has an acoustic signal generator to output a measurement result.

15. A method for determining an optical property of a plant by means of a reflection measurement, wherein light in a first wavelength range is emitted along a first beam axis by means of a first light source, and light in a second wavelength range is emitted along a second beam axis by means of a second light source, wherein light reflected from the plant is detected by at least one first receiver, which is aligned along a third beam axis, wherein the first light source, the second light source, and the at least one first receiver are arranged relative to one another in such a manner that a target cylinder of the first light source extending along the first beam axis, a target cylinder of the second light source extending along the second beam axis, and a first measuring cylinder, which extends along the third beam axis, at least partially overlap one another in a measuring space, and the first beam axis and the second beam axis respectively enclose an angle with the third beam axis, and wherein the target cylinder of the first light source and the target cylinder of the second light source in the measuring space each have a diameter of approximately 1 mm to approximately 6 mm, wherein the measuring cylinder of the at least one receiver in the measuring space has a diameter of approximately 8 mm.

16. The sensor system as claimed in claim 3, wherein the first light source and the second light source each emit light pulsed in a constant frequency, wherein the frequencies are different from one another, wherein the first receiver analyzes signals which have the frequency of the first light source, and wherein the second receiver analyzes signals which have the frequency of the second light source.

17. A sensor system for determining an optical property of a plant by means of a reflection measurement, having a first light source, which emits light along a first beam axis, and a second light source, which emits light along a second beam axis, and at least one first receiver, which is aligned along a third beam axis, to detect light reflected from the plant, wherein the first light source, the second light source, and the at least one first receiver are arranged relative to one another in such a manner that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle with the third beam axis, wherein the first light source emits light in a first wavelength range and the second light source emits light in a second wavelength range, wherein the first wavelength range is a wavelength range of green light, wherein the second wavelength range is a wavelength range of red light, wherein the first light source and the second light source are arranged in a first housing, and the at least one first receiver is arranged in a second housing separate from said first housing, and a fastening mechanism connecting the first housing to the second housing, wherein the fastening mechanism enables the adjustment of the distance between the first housing and the second housing.

18. A sensor system for determining an optical property of a plant by means of a reflection measurement, having a first light source, which emits light along a first beam axis, and a second light source, which emits light along a second beam axis, and at least one first receiver, which is aligned along a third beam axis, to detect light reflected from the plant, wherein the first light source, the second light source, and the at least one first receiver are arranged relative to one another in such a manner that a target cylinder, which respectively extends along the first beam axis and the second beam axis, and a first measuring cylinder, which extends along the third beam axis, at least partially overlap one another in a measuring space, and the first beam axis and the second beam axis respectively enclose an angle with the third beam axis, wherein the first light source emits light in a first wavelength range and the second light source emits light in a second wavelength range, wherein the first wavelength range is a wavelength range of green light, wherein the second wavelength range is a wavelength range of red light, wherein the first light source and the second light source are arranged in a first housing, and the at least one first receiver is arranged in a second housing separate from said first housing, and a fastening mechanism connecting the first light source, the second light source and the at least one first receiver, wherein the fastening mechanism enables the adjustment of the angles between the beam axes of the light sources and the beam axis of the at least one first receiver.

* * * * *